(12) United States Patent
Chen

(10) Patent No.: US 6,582,583 B1
(45) Date of Patent: Jun. 24, 2003

(54) AMPEROMETRIC BIOMIMETIC ENZYME SENSORS BASED ON MODIFIED CYCLODEXTRIN AS ELECTROCATALYSTS

(75) Inventor: Ellen T. Chen, Germantown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/451,141

(22) Filed: Nov. 30, 1999

Related U.S. Application Data

(60) Provisional application No. 60/110,470, filed on Nov. 30, 1998.

(51) Int. Cl.[7] .......................... C25D 11/00; G01N 33/50
(52) U.S. Cl. .............. 205/317; 205/198; 204/403.01; 204/415; 204/418; 435/287.2; 435/287.9; 435/817; 422/82.03
(58) Field of Search ........................... 204/418, 403.01, 204/415; 205/198, 317; 435/817, 287.2, 287.9; 422/82.03

(56) References Cited

U.S. PATENT DOCUMENTS

| | | |
|---|---|---|
| 4,151,049 A | 4/1979 | Janata |
| 4,240,889 A | 12/1980 | Yoda et al. |
| 4,269,674 A | 5/1981 | Osa et al. |

(List continued on next page.)

FOREIGN PATENT DOCUMENTS

| | | |
|---|---|---|
| JP | 55-85683 | 6/1980 |
| JP | 55-85684 | 6/1980 |
| JP | 60-93340 | 5/1985 |
| JP | 63-256679 | 10/1988 |
| JP | 03-248057 | 11/1991 |
| JP | 03-273003 | 12/1991 |
| JP | 04-52546 | 2/1992 |
| JP | 04-2869950 | 10/1992 |
| JP | 04-313047 | 11/1992 |
| JP | 05-312746 | 11/1993 |
| JP | 07-27690 | 1/1995 |

OTHER PUBLICATIONS

Alarie, J.P., V–DINH, T. Talanta, 1991, 38(5), 529–534.
Bucke, C. Polysaccharide Biotechnology–a Cinderall Subject, Trends in Biotech. 1998 16(2), 50–52.
Chen, E. T. Dissertation of Ph.D. Title "A Study of Analytical Application of the Catalytic Properties of Cyclodextrons" 1994.
Chen, E.T., Pardue, H.L. "Analytical Application of Catalytic Properties of Modified Cyclodextrins" Anal Chem. 1993, 65, 2563–2567.
Chen, Q. Novel Designs and Fabrication of Amperometric Biosensors (Enzymes, glucose strips) Dissertation, DAI, 57, No. 01B, (1995), 0286.
Chung, C. Dissertation of Ph.D. Title "Spontaneously Adsorbed Monolayer Films: Fabrication, Characterization, and Application of Monolayers of Alkanethiol and Suilfur–bearing," 1990.
Dagani R., "The Shape of Things to Come. Materials Symposinm Spotlights Progress in the Creation of Supramolecular Assemblies, Nanostructures an Devices" C & EN. Jun. 8, 1998, 35–46.

(List continued on next page.)

*Primary Examiner*—Lyle A. Alexander
*Assistant Examiner*—Monique T. Cole
(74) *Attorney, Agent, or Firm*—Venable; Keith G. Haddaway

(57) ABSTRACT

The present invention provides a novel biosensor for the detection of chemicals of interest. The novel biosensor of the present invention comprises an electrode having a catalytically active cyclodextrin attached thereto. The present invention will be useful for the detection of materials in a wide variety of samples. In particular, the present invention will permit the detection of nitrophenyl esters.

31 Claims, 14 Drawing Sheets mM-β-DMCD

U.S. PATENT DOCUMENTS

| | | | |
|---|---|---|---|
| 4,420,564 A | 12/1983 | Tsuji et al. | |
| 4,495,036 A | 1/1985 | So | |
| 4,525,704 A | 6/1985 | Campbell et al. | |
| 4,655,900 A | 4/1987 | Neti et al. | |
| 4,662,996 A | 5/1987 | Venkatasetty | |
| 4,832,797 A | 5/1989 | Vadgama et al. | |
| 4,906,376 A | 3/1990 | Fyles | |
| 4,948,727 A | 8/1990 | Cass et al. | |
| 4,957,615 A | 9/1990 | Ushizawa et al. | |
| 5,112,471 A | 5/1992 | Shibata et al. | |
| 5,118,405 A | 6/1992 | Kaneko et al. | |
| 5,120,420 A * | 6/1992 | Nankai et al. | 204/403 |
| 5,160,418 A | 11/1992 | Mullen | |
| 5,225,064 A | 7/1993 | Henkens et al. | |
| 5,242,793 A | 9/1993 | Kariyone et al. | |
| 5,244,562 A | 9/1993 | Russell | |
| 5,286,364 A | 2/1994 | Yacynych et al. | |
| 5,288,613 A | 2/1994 | Luong et al. | |
| 5,332,479 A | 7/1994 | Uenoyama et al. | |
| 5,342,490 A | 8/1994 | Lever et al. | |
| 5,352,574 A | 10/1994 | Guiseppi-Elie | |
| 5,354,679 A | 10/1994 | Ohashi | |
| 5,376,251 A | 12/1994 | Kaneko et al. | |
| 5,411,866 A | 5/1995 | Luong et al. | |
| 5,418,058 A * | 5/1995 | Li et al. | 428/327 |
| 5,425,869 A | 6/1995 | Noding et al. | |
| 5,432,274 A | 7/1995 | Luong et al. | |
| 5,443,706 A | 8/1995 | Kuroda et al. | |
| 5,480,924 A | 1/1996 | Vieil et al. | |
| 5,505,836 A | 4/1996 | Miyahasra et al. | |
| 5,506,420 A | 4/1996 | Kossovsky et al. | |
| 5,512,159 A * | 4/1996 | Yoshioka et al. | 204/403 |
| 5,531,871 A | 7/1996 | Fauteux et al. | |
| 5,538,655 A | 7/1996 | Fauteux et al. | |
| 5,540,828 A * | 7/1996 | Yacynych | 204/418 |
| 5,587,466 A | 12/1996 | Vieil et al. | |
| 5,605,617 A | 2/1997 | Bidan et al. | |
| 5,609,749 A | 3/1997 | Yamauchi et al. | |
| 5,624,537 A | 4/1997 | Turner et al. | |
| 5,658,443 A | 8/1997 | Yamamoto et al. | |
| 5,667,662 A | 9/1997 | Sonnenberg et al. | |
| 5,755,939 A | 5/1998 | Dror et al. | |
| 6,051,389 A * | 4/2000 | Ahl et al. | 435/10 |
| 6,099,804 A * | 8/2000 | Clausen et al. | 422/82.01 |

OTHER PUBLICATIONS

EMR, S. Use of Polymer Films in Amperometric Biosensors and Chemically Modified Electrodes, DAI, 56, No. 07B, (1995), 3728.

Gregg, B.A. Heller, A. "Redox Polymer Films Containing Enzynes. Z. Glucose Oxodase Containing Enzyme Electrodes." Phys. Chem. 1991, 95, 5976–5908.

Groom, Carl A. et al., Dual Functionalities of 4–Aminodiphenylamine in Enzymatic Assay and Mediated Biosensor Construction, Analytical Biochemistry, 231, 393–399 (1995).

Ikeda, H., et al., "Artificial Hydralase Using Modified Dimethyl–B–Cycloddextrin" J. Inclusion Phenom. 1989, 7, 117–124.

Iwakura, Y. et al. "The Sterochemically Correct Catalytic Site on Cyclodextrin Resulting In A Better Enzyme Model" J. Amer. Chem. Soc. 1975, 97, 4432–4434.

Kataky, R. and D. Parker, Analyst, Dec. 1996, vol. 121, 1829–1834, Sensitive and Specific Electrochemical Sensors for Charge–Diffuse cations: Use of Lipophilic Cyclosdextrins and an Enzyme Relay for the Determination of Acetylcholine.

Kataky, R., D. Parker, P.M. Kelly, Potentiometric Enantioselective Sensors for alkyl and Aryl Ammonium Ions of Pharmaceutical Significance, Based on Lipophilic Cyclodextrims, Scan. J. Clin. Lab. Invest. 1995, 55, 409–419.

Kojima, M. et al J. Chem. Soc. Perkin Trans 1981, 1, 1647–1651

Koradecki, D., et al., "Inclusion of the Region Isomeric Nitrobenzene Derivateives and Ferrocene Guests by B–cyclodextrin Polymer and The Polymer Matrix." Inc. Phenom. 1991, 10, 79–96.

Kotte, H., et al., "Methylphenazonium–Modified Enzyme Sensor Based on Polymer Thick Films for Subnanomolar Detection of Phenols" Anal. Chem. 1995, 67, 65–70.

Lehn, J. M. "Supramolecular Chemistry: Receptors, Catalysts, and Carriers." Science, 1985, 227, 849–856.

Li, G., McGown L. B. Dissertation Abstracts International. 1994, 785–B–786–B.

Li, G., McGown, L. B. "Molecular Nanotube Aggregates of β– and λ–Cyclodextrins Linked by Diphenyl–hexatrienes." Science, 1994, 264, 249–251.

Lim, K. B., Pardue, H. L. "Highly Rugged Kinetic Method for The Enzymatic Determination of DNA in Agorose Gel With Array Detection Using A Charge Coupled Device." Anal. Chim. Acta, 1996, 329, 285–295.

Liu, H., et al., "Amperometric biosensor sensitive to glucose and lactose based on co–immobilization of ferrocene, glucose oxidase, B–galactosidase and mutarotase in B–cyclodextrin polymer". Analytica. Chimica Acta, 1998, 358, 137–144.

Luong, JH et al, Characterization of interacting ferrocene–cyclosdextrin systems and their role in mediated bisensors, J. Mol. Recognit. 1995, Jan. 8 (1–2), 132–138.

Luong, JH et al, Monitoring the Activity of Glucose Oxidase During the Cultivation of Aspergillus Niger using Novel Amperometric Sensor with 1,1'–dimethylferricinuim as a Mediator, Biosens Bioelectron., 1994 9(8), 577–584.

Luong, John H.T., et al., Enzyme reactions in the presence of cyclodextrins: biosensors and enzyme assays, Trends in Biotechnology, Nov. 1995, vol. 13, pp. 457–463.

Markowitz, M. A., et al., J. Am. Chem. Soc., 1988, 110, 7546–7546.

Nagy, Zoltan, Electrochemistry Dictionary, http://electrochem.cwru.edu/ed/dict.htm, Dec. 21, 2001.

Nuzzo, R. G., et al., J. Am. Chem. Soc. 1987, 109, 2358–2368.

Pardue, H. L. "Kinetic Aspect of Analytical Chemistry" Anal. Chim. Acta, 1989, 216, 69–107.

Proceedings of the NATO Advanced Reserach Workshop on Chemosensors of Ion and molecular Recognition, Kluwer Academic Publishers, Bonas, France, 1997.

Ross, et al. "The Accuracy of Laboratory Measurements in Clinical Chemistry. A Study of 11 Routine Chemical Analytes In The College of American Pathologists Chemistry Survey with Fresh Frozen Serum, Definitive Methods, and Reference Methods." Arch. Path.

Szejtli, J. Cyclodextrin Technology, Kluwer Academie Publishers, Boston, 1988, pp. 365–368, 396–401, 432–434.

Valsami, G.N., et al., Complexation Studies of Cyclodexatrins with Tricyclic Antidepressants using Ion–Selective Electrodes, Pharmaceuticals Research, Jan. 1992, 9(1) pp. 94–100.

Valsami, Georgia N., et al., Binding Studies of Ions with Cyclosdextrins Using Ion–Selective Electrodes, J. of Pharmaceutical Sciences, vol. 79, No. 12, Dec. 1990.

Wang, J. et al., Sequence specific electrochemical biosensing of M. Tuberculosis DNA, Anal. Chim. Acta 1997, 337:41–48.

Wang, X., Pardue, H. L. "Improved Ruggedness for Membrane–Based Amerometric Sensors Using A Pulsed Amperometric Method." Anal. Chem. 1997, 69, 4482–4489.

Williams, M., et al., "Measurement/data–processing method to improve the ruggedness of membrane–based sensors: Application to amperometric oxygen sensor" Talanta, 1996, 43, 1379–1385.

Zhao, S., Luong, H. Y. "Bioelectocatalysis of water–soluble tetrathiafulvalene–z–hydroxypropyl–B–Cyclodextrin Cyclodextrin complex" Analytica. Chimica Acta, 1993, 282, 319–327.

* cited by examiner mM-β-DMCD

PVP: Poly(4-vinylpyridine)

PEG: Polyethylene glycol diglycidyl ether

AMPEROMETRIC BIOMIMETIC ENZYME SENSORS BASED ON MODIFIED CYCLODEXTRIN AS ELECTROCATALYSTS

This nonprovisional application claims the benefit of U.S. Provisional Application No. 60/110,470 filed Nov. 30, 1998.

This work was supported in part by Grant No. GM 13326-26 from National Institutes of Health.

BACKGROUND OF THE INVENTION

The following references are incorporated herein in their entirety by reference: Certa, H., Fedtke, N., Wiegand. H. J., Miller, A. M. F., Bolt, H. M. *Arch. Toxicol.* 1996, 71, 112–122; EPA method 604, Phenols in Federal Register, Oct. 26, 1984. Environment Protection Agency, Part VIII, 40 CFR Part 136, 58–66; EPA method 625, Base/neutrals and acids in Federal Register, Oct. 26, 1984. Environment Protection Agency, Part VIII, 40 CFR Part 136, 154–174; Puig, D., Barceló. *Trends in Anal. Chem,* 1996, 15(8), 362–375; Li, N., Lee, H. K. *Anal. Chem.* 1997, 69, 5193–5199; Bender, M. L., Komiyama, M. *Cyclodextrin Chemistry*, Springer-Veriag, Berlin, 1978; Breslow, R., Bovy, P., Hersh, C. L. *J. Am. Chem. Soc.* 1980, 102, 2115; Szejtli, J. *Cyclodextrin Technology*, Kluwer Academie Publishers, Boston, 1988; Editor Sant'e, D. *Minutes of the Sixth International Symposium on Cyclodextrins*, Paris, 1992; Editor Bethell, D. *Advances in Physical Organic Chemistry*, 1994, Volume 29, 1–85, Academic Press. New York; Chen, E. T., Pardue, H. L. *Anal. Chem.* 1993, 65, 2583–2587; Ikeda, H., Kojin, R., Yoon, C.-L., Ikeda, T., Toda, F., *J. Inclusion Phenom.* 1989, 7, 117–124; Chen, E. T. unpublished cytotoxicity report of the mM-β-DMCD; Alarie, J. P., Vo-Dinh,T. *Talanta,* 1991, 38(5), 529–534; Zhao, S., Luong, H. Y. *Analytica. Chimica Acta,* 1993, 282, 319–327; Liu, H., Li, H., Ying, T., Sun, K., Qin, Y., Qi, D. *Analytica. Chimica Acta,* 1998, 358, 137–144; Li, G., Mcgown L. B. *Dissertation Abstracts International.* 1994, 56/02-B; Li, G., Mcgown, L. B. *Science,* 1994, 264, 249–251; Mallouk, T. E., Harrison, D. J. (editors) *Interfacial Design and Chemical Sensing,* 1994, ACS Symposium Series 561; Roberts, S. M. *Molecular Recognition, Chemical and Biochemical Problems*, Royal Society of Chemistry, 1989; Chidsey, C. E. D. *Science,* 1991, 251, 919–922; Nuzzo, R. G., Fusco, F. A., Allara, D. L. *J. Am. Chem. Soc.* 1987, 109, 2358–2368; Spasov, A. *Ann. Univ. Sufia, II Faculte Phys. Math. Livre,* 1939, 2(35), 289–291; Chen, E. T. *Dissertation of Ph.D. Title "A Study of Analytical Application of the Catalytic Properties of Cyclodextrons"* 1994; Chung, C. *Dissertation of Ph.D. Title "Spontaneously Adsorbed Monolayer Films: Fabrication, Characterization, and Application of Monolayers of Alkanethiol and Sulfur-bearing"*, 1990; Markowitz, M. A., Bielski, R., Regen, S. L. *J. Am. Chem, Soc.,*1988, 110, 7545–7546; Gregg, B. A., Heller, A. *J. Phys. Chem.* 1991, 95, 5976–5980; Komiyama, M. *Ange. Macromole. Chemie,* 1988, 163, 205–207; Koradecki, D., Kutner, W. *J. Incl. Phenom.* 1991, 10, 79–96; Lehn, J. M. *Science,* 1985, 227, 849; *Proceedings of the NATO Advanced Research Workshop on Chemosensors of Ion and Molecular Recognition*, Kluwer Academic Publishers, Bonas, France, 1997; (Editors) Scheller, F. W., Schubert, F., Fedrowitz, J. *Frontiers in Biosensorics*, (books one and two), Birkh-user Verlag Base, Boston, 1997; Szejtli, J., Szente, L. *Proceedings of the Eighth International Symposium on Cyclodextrins*, Budapest, Hungary, Kluwer Academic Publishers, Boston, 1996; Dagani, R. C & EN. Jun. 8, 1998, 35–46; Pardue, H. L. *Anal. Chim. Acta,* 1989, 216, 69–107; Williams, M., Pardue, H. L, Uhefbu, C. E., Smith, A. M., Studley, J. *Talanta,* 1996, 43, 1379–1385; Lim, K. B., Pardue, H. L. *Anal. Chim. Acta,* 1996, 329, 285–295; Wang, X., Pardue, H. L. *Anal. Chem.* 1997, 69, 4482–4489; Kotte, H., Grundig, B., Vortop, K-D., Strehlitz, B., Stottmeister,U. *Anal. Chem.* 1995, 67, 65–70; Bucke, C. Polysaccharide biotechnology-a Cinderella subject, *Trends in Biotech.* 1998, 16(2), 50–52; Ross, et al. *Arch. Pathol. Lab. Med.* 1998, 122:587–608; Wang, J. *Anal. Chim. Acta* 1997, 337:41; and *Biosensors and Electronic Noses*, Kres-Roger, Editor, CRC Press, N.Y., 1997.

FIELD OF THE INVENTION

The present invention relates to the field of biosensors and, in particular, to biosensors comprising a catalytically active cyclodextrins.

DESCRIPTION OF RELATED TECHNOLOGY

Many chemicals in common use in industrialized societies contain aromatic esters. Examples of the types of chemicals containing aromatic esters include detergents, antioxidants and agricultural chemicals. Upon degradation of these aromatic esters whether through enzymatic hydrolysis or bacterial degradation, toxic phenols and phenol derivatives are produced. Research has shown that these toxic chemicals can accumulate in food, soil, and water. In addition, it has been shown that the presence of these chemicals can be dangerous to humans and animals as they can have adverse effects on reproduction and have been implicated in the development of tumors (Certa et al. 1996). The United States Environmental Protection Agency (US-EPA) has listed phenolic compounds as priority pollutants due to their toxicity and persistence in the environment (EPA method 604, Phenols in Federal Register, Oct. 26, 1984, Environment Protection Agency, Part VIII, 40 CFR Part 136, 58–66; EPA method 625, Base/neutrals and acids in Federal Register, Oct. 26, 1984. Environment Protection Agency, Part VIII, 40 CFR Part 136, 154–174). Furthermore, European Community Directive 76/464/EEC recommends that the maximum level of phenolic compounds in surface water for drinking purposes should be in the 1–10 $\mu$g/L range (Puig et al.). Therefore, developing a sensitive, reliable, and fast testing method for the detection of phenolic compounds is an issue of importance to the entire industrialized world.

Current methods for the detection of phenolic compounds include liquid chromatography with electrochemical (LCEC) detection and a coupled gas chromatography/mass spectrometry (GC/MS) method which requires sample pretreatment (Puig et al. 1996; Li et al. 1997). These currently employed methods suffer from various limitations. For example, the LCEC method is subject to interference because of the high applied potential (around 1V) required for electrochemical detection of the phenolic compounds. The high polarizing potential causes oxidation of other matrix compounds; hence, an increase in background current is frequently observed. In addition, the LCEC method has problems with signal stability, pH dependence, and time consuming experimental protocols. The GC/MS method usually requires sample derivatization prior to analysis. For example, Li and co-workers (Li et al. 1997) converted phenols to phenyl acetate prior to analyzing with GC/MS. It has been suggested by Puig (Puig et al. 1996) that the US-EPA method for derivatization of nitrophenols for GC/MS may often lead to incorrect results.

Conventional electrochemical methods used to detect toxic phenols suffer from signal drift, and the probes need frequent cleaning because of polymerization caused by oxidation of phenols (Puig et al. 1996). Because traditional electrochemical methods are sensitive to pH they have limited practical application. To date, no satisfactory approach exists for measuring phenols. Cyclodextrins (CDs) and modified CDs have been used as biomimetic enzyme (BMZ) catalysts for several decades (Bender et al. 1978; Breslow et al. 1980; Szejtli et al. 1988; Editor Sant'e, D. *Minutes of the Sixth International Symposium on Cyclodextrins*, Paris, 1992; Editor Bethell, D. *Advances in Physical Organic Chemistry*, 1994, Volume 29, 1–85, Academic Press, N.Y.). CDs are cyclic carbohydrates made up of six (α-CD), seven (β-CD) or eight (γ-CD) linked D-glucopyranose units. They look like hollow truncated cones, where the interior cavity is hydrophobic and the outside is hydrophilic. The cavities can entrap a variety of chemicals having suitable size and hydrophobicity. Functional groups can be attached to the CDs enabling them to mimic enzyme catalysis. For example, one or two imidazolyl groups attached on the C-3 position of the dimethyl-β-cyclodextrin (β-DMCD) can enhance catalysis of the hydrolysis of paranitrophenyl acetate (p-NPA) to para-nitrophenolate (p-NPO⁻) with rate increases up to several thousand times the un-catalyzed rate (Chen et al. 1993; Ikeda et al. 1989). The nomenclature used to identify the imidazole modified β-DMCDs is mM-β-DMCD for mono-imidazolyl substituted β-DMCD and bM-β-DMCD for bis-imidazolyl substituted β-DMCD. The M before β in the abbreviation represents imidazolyl group. mM-β-DMCD has been used in solution to mimic the natural enzyme β-chymotrypsin. The protease β-chymotrypsin has a pH optimum of 8.2 for the hydrolysis reaction of p-NPA and achieves only a modest rate acceleration at this pH. In contrast, mM-β-DMCD can work at wide range of pH values. In addition, these modified CDs have good stability, and have unique solubility in both aqueous and organic phases. The mM-β-DMCD showed good selectivity for p-NPA and the cytotoxicity of mM-β-DMCD has been studied (Chen et al. 1993; Ikeda et al. 1989; Chen, E. T. unpublished cytotoxicity report of the mM- -DMCD).

Biosensors of the prior art generally contain immobilized enzymes on the surface of an electrode. This type of biosensor has found application for the detection of various analytes. Systems of this type generally include a mediator that functions to shuttle electrons from the electrode to the electrochemically active species detected. The biosensors of the prior art based on immobilized enzymes have a major flaws in that the response time is dependent upon the concentration of the analyte and the requirement for a mediator introduces an additional complexity and source of error.

New types of biosensors have been developed utilizing CDs and CD derivatives. The unique properties of CDs have been used to enhance the performance of biosensors with both optical and electrochemical detection. Examples of the use of CDs in sensors are provided by U.S. Pat. No. 5,540,828 to Yacynych, U.S. Pat. Nos. 5,587,466 and 5,480,924 issued to Vieil, et al. and U.S. Pat. No. 5,432,274 issued to Luong, et al., the specifications of which are specifically incorporated herein by reference. A variety of analytes can be detected in a fast, selective and sensitive way using CDs. Alarie and co-workers have developed a fiber-optic CD-based fluorescence sensor that utilized CDs' inclusion property to detect pyrene (Alarie et al. 1991). When using traditional electrochemical methods, electron mediators are needed in most cases; however, most of the mediators are toxins. Luong and co-workers used modified CDs to form a water soluble complex with tetrathiafulvalene (TTF) and used the complex as an electron mediator for a glucose biosensor (Zhao et al. 1993). The inclusion property of CDs was used in the development of an amperometric glucose biosensor as reported by Liu and coworkers (Liu et al. 1998). Recently, CDs, together with inclusion compounds, were found to form molecular nanotubes through self-assembly (Li et al., *Dissertation Abstracts International* 1998; Li et al., Science 1994). Molecular self-assembly technology for developing membranes is recognized as superior to conventional techniques because it can provide varying degrees of spatial and orientation arrangements of amphiphilic molecules on variety of surfaces of substrates as reported elsewhere (Mallouk et al. 1994; Roberts 1989; Chidsey 1991; Nuzzo et al. 1987). The formation of nanotubes made with CD and diphenylhexatriene based on the molecular inclusion has reported in the literature (Le et al. 1994).

One analytical technique which may be used in conjunction with a biosensor is cyclic voltammetry. In cyclic voltammetry, the potential of the electrode is scanned linearly from an initial value to a second value and then back to the initial value or some other potential. As the potential is scanned in the positive direction, an anodic current occurs when the electrode becomes a sufficiently strong oxidant to oxidize the analyte. The anodic current increases rapidly until the concentration of the analyte on the electrode surface approaches zero corresponding to a peak in the current. The current then decays as the solution surrounding the electrode is depleted of the analyte due to the conversion of the analyte into an oxidized form. When the highest potential of the scan is reached, the potential is scanned in the negative direction. When the electrode becomes a sufficiently strong reductant, the oxidized form of the analyte is reduced back to the original form. This reduction causes a cathodic current that increases until the concentration of the oxidized form of the analyte on the electrode approaches zero at which point the current peaks. The cathodic current then decays as the solution of the in the vicinity of the electrode is depleted of the oxidized form of the analyte. The cycle is completed when the potential returns to the initial value or to another predetermined potential value. Additional scans may then be made. When the oxidized form of the analyte is not reduced during the scan back to the starting potential, the reaction is said to be irreversible. The parameters determined in a cyclic voltammogram are the magnitude of the anodic peak current, $i_{pa}$, the anodic peak potential, $E_{pa}$, the cathodic peak current, $i_{pc}$, and the cathodic peak potential, $E_{pc}$. The pseudo first order rate constants can be obtained from plots of the $\ln(i_\infty - i_t)$ where $i_\infty$ is the maximum current and $i_t$ is the current at time t.

Notwithstanding the above mentioned uses of CDs, utilizing the catalytic and molecular recognition features of mM-β-DMCD for biosensor development is difficult for the following reasons: (1) low coverage due to the monolayer defects, (2) low sensitivity and (3) low reproducibility as reported in the literature (Chung 1990; Gregg et al. 1991; Komiyama 1988; Koradecki et al. 1991). Thus, there exists a need in the art for a biosensor specific for phenolic compounds. In addition, there exists a need in the art for biosensors that do not utilize electron mediator molecules. These and other needs have been met by the present invention.

OBJECTS OF THE INVENTION

It is an object of the present invention to provide a novel biosensor. In preferred embodiments, the biosensor of the present invention may comprise an electrode and a catalytically active cyclodextrin affixed thereto.

It is an object of the present invention to provide a biosensor specific for the detection of phenolic compounds. In preferred embodiments, the biosensor of the present invention may comprise a β-DMCD comprising one or more imidazole groups. In a most preferred embodiment, the biosensor of the present invention may comprise a mM-β-DMCD.

It is an object of the present invention to provide a biosensor capable of detecting molecules of interest that does not require the inclusion of a mediator.

It is an object of the present invention to provide a method for detecting an analyte of interest comprising the steps of contacting a solution containing the analyte with a biosensor and detecting the analyte wherein the biosensor comprises a catalytically active cyclodextrin.

It is an object of the present invention to provide a method of detecting the presence of o-NPA in solution comprising the step of contacting a solution containing o-NPA with a biosensor, which biosensor comprises a catalytically active cyclodextrin. In preferred embodiments, the cyclodextrin may be mM-β-DMCD.

SUMMARY OF THE INVENTION

The present invention provides a novel biosensor comprising an electrode with a catalytically active cyclodextrin attached thereto. In a preferred embodiment, the novel biosensor of the present invention comprises a modified cyclodextrin capable of catalyzing the hydrolysis of NPA thereby making possible the measurement of nitrophenyl acetate (NPA) without the use of an electron mediator. In other preferred embodiments, the catalytically active cyclodextrins of the present invention may be assembled in the form of nanotubes.

The electrode of the present invention may be constructed of any material customarily used by those skilled in the art for the construction of electrodes. In preferred embodiments, the electrode may be glassy carbon, gold or silver. In a most preferred embodiment, the electrode may be glassy carbon.

The biosensor of the present invention may be constructed by coating the surface of an electrode with a catalytically active cyclodextrin to form a membrane. This coating may be accomplished by any means known by those skilled in the art. In addition to a cyclodextrin, the electrode may be coated with one or more compounds. In preferred embodiments, the electrode may be coated with a catalytically active cyclodextrin and a polyethylene glycol (PEG). In another preferred embodiment, the electrode may be coated with a catalytically active cyclodextrin, a PEG and a polyvinylpyridine (PVP). In a most preferred embodiment, the cyclodextrin will be deposited in the form of nanotubes and will be applied by co-polymerization of mM-β-DMCD with polyethylene glycol diglycidyl ether (PEG) and poly (4-vinylpyridine) (PVP).

Panel A shows the results obtained with o-NPA, Panel B shows the results obtained with p-NPA and Panel C shows the results obtained with m-NPA, Panel D shows the results of o-NPA with an un-coated glassy carbon electrode.

Figure 8:
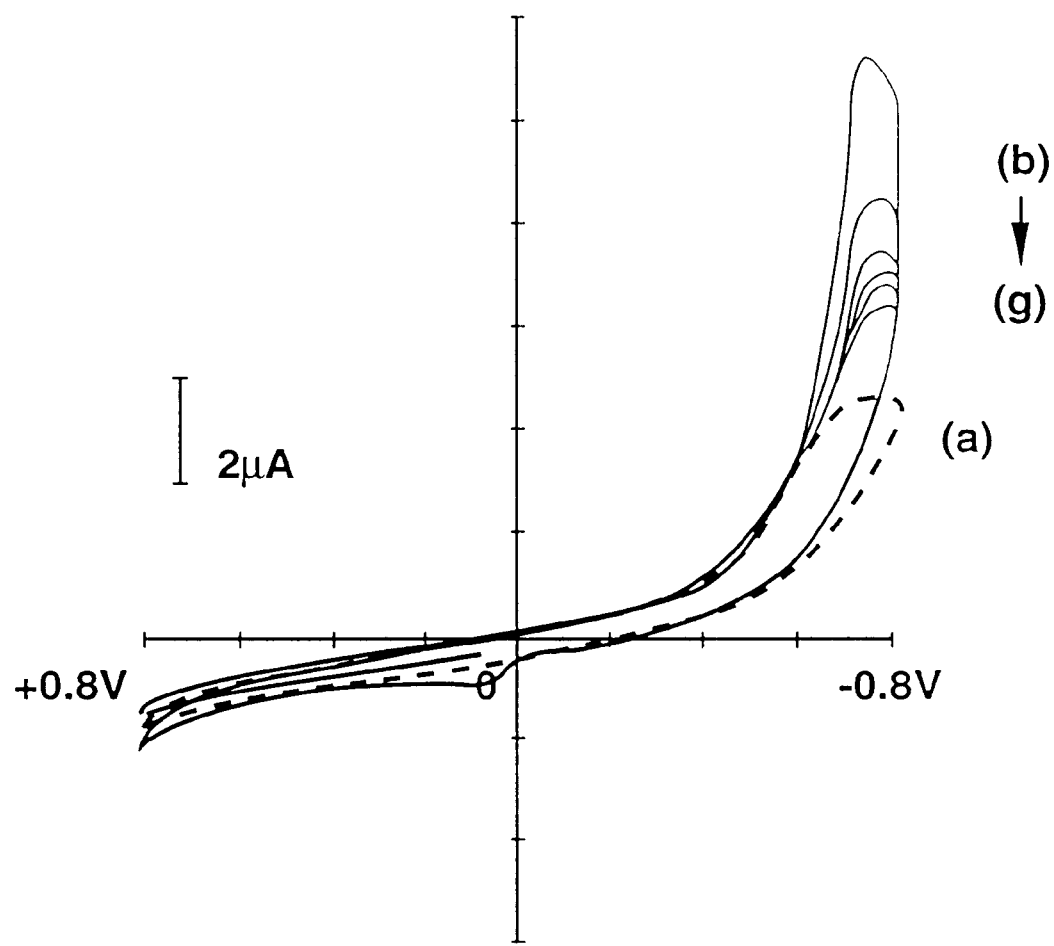

FIG. 8. Cyclic voltammogram of o-NPA obtained with a two component sensor.

Figure 9:
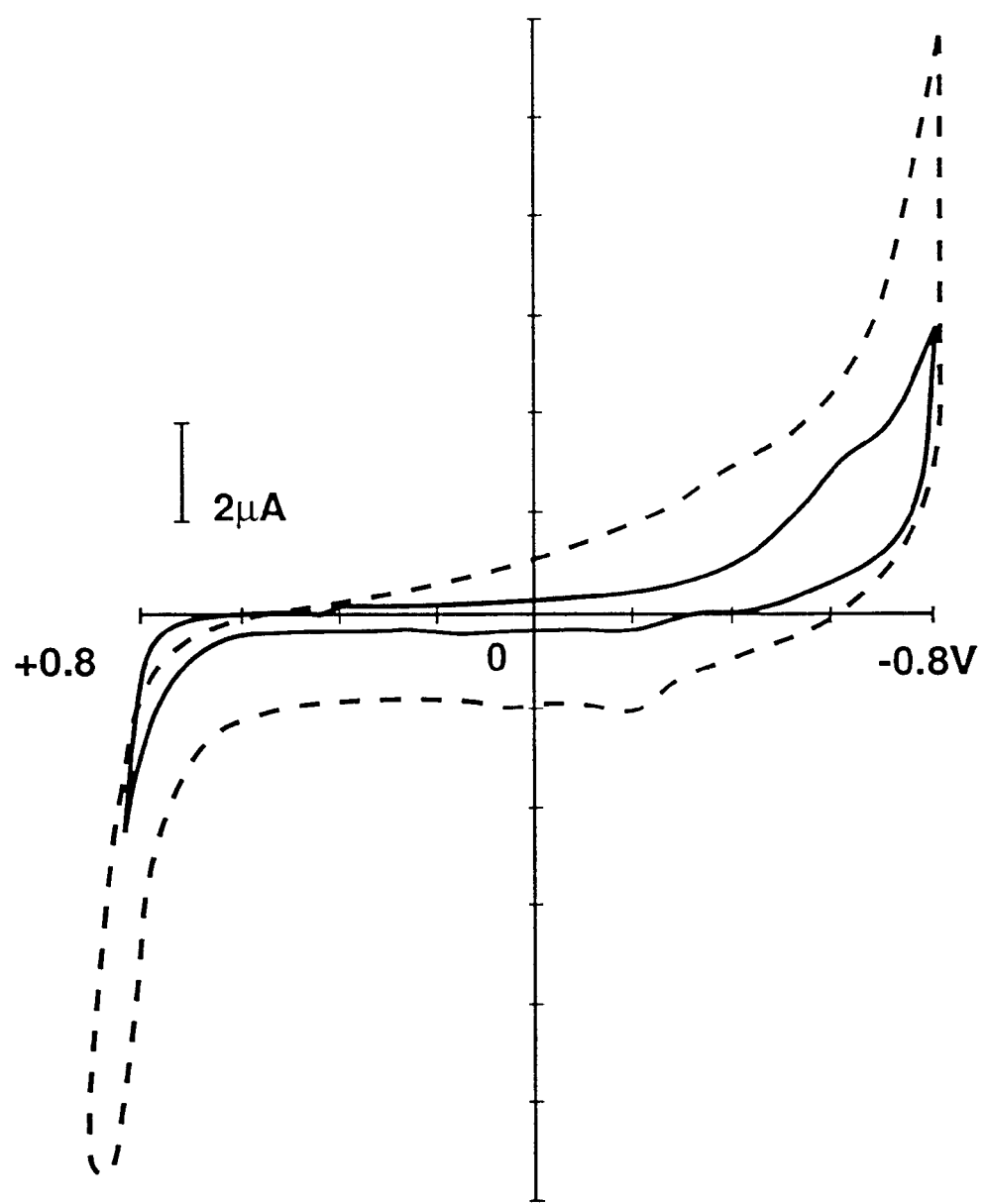

FIG. 9. Cyclic voltammogram of o-NPO$^-$ obtained with a three component sensor.

Figure 10:
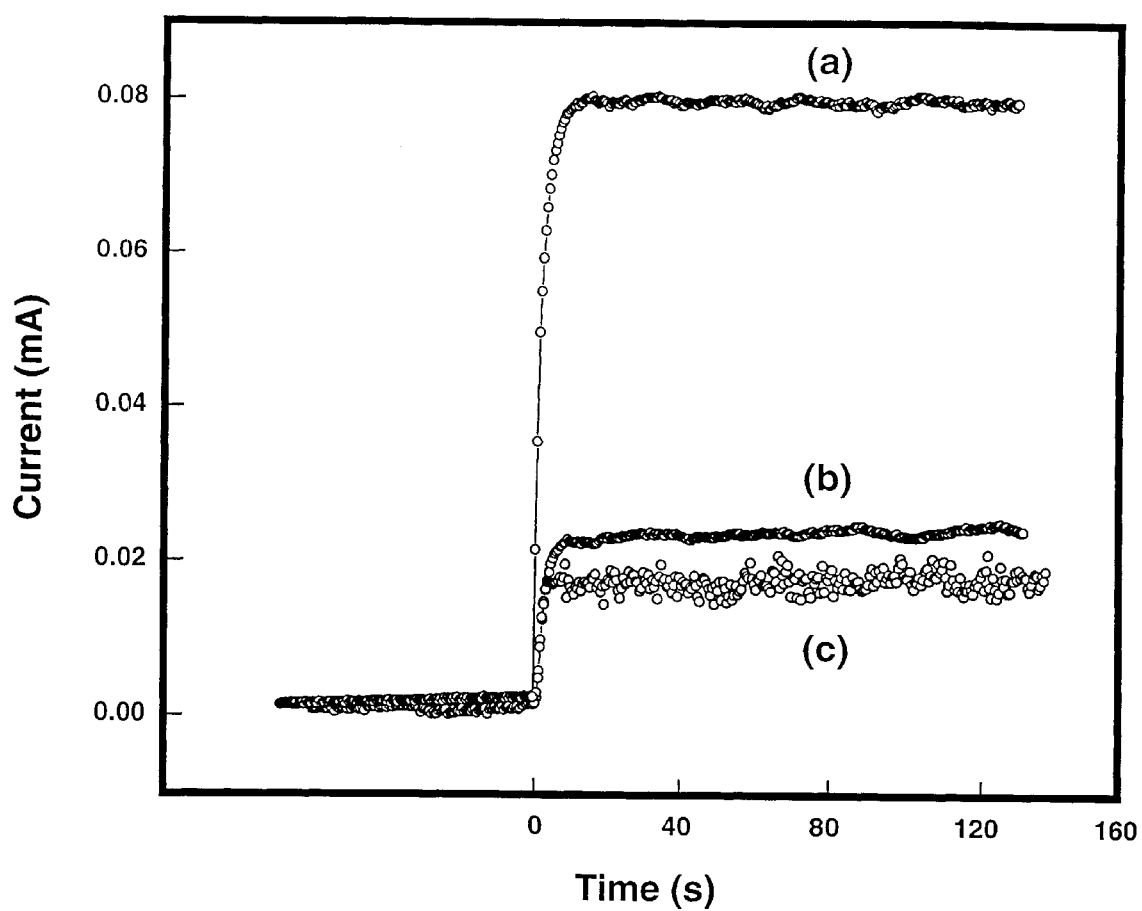

FIG. 10. Amperometric response curve showing bare electrode response to o-NPO$^-$ and response of three component sensor to o-NPA and o-NPO$^-$.

Figure 11:
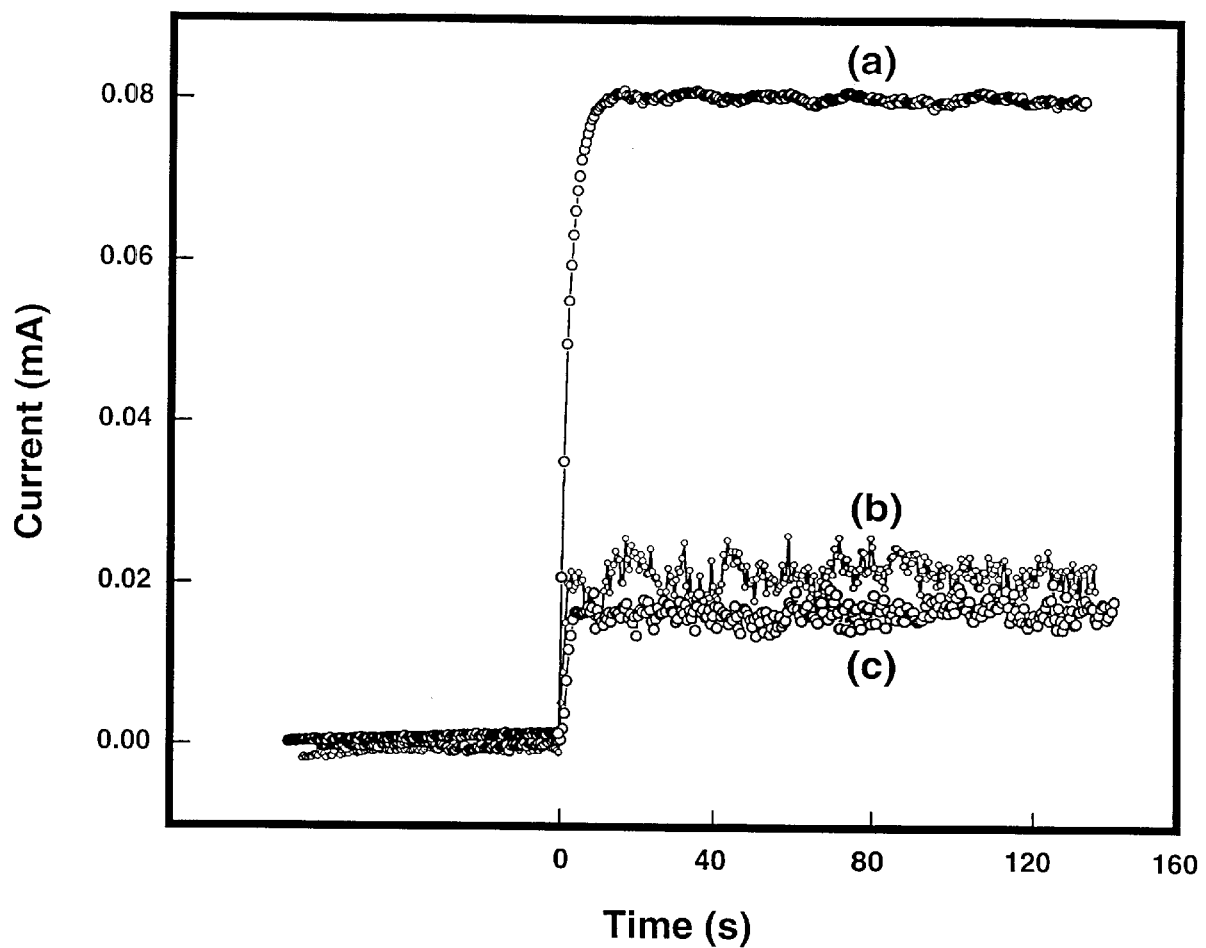

FIG. 11. Amperometric response curve showing response of bare electrode to o-NPA and o-NPO$^-$ and three component sensor response to o-NPA.

Figure 12:
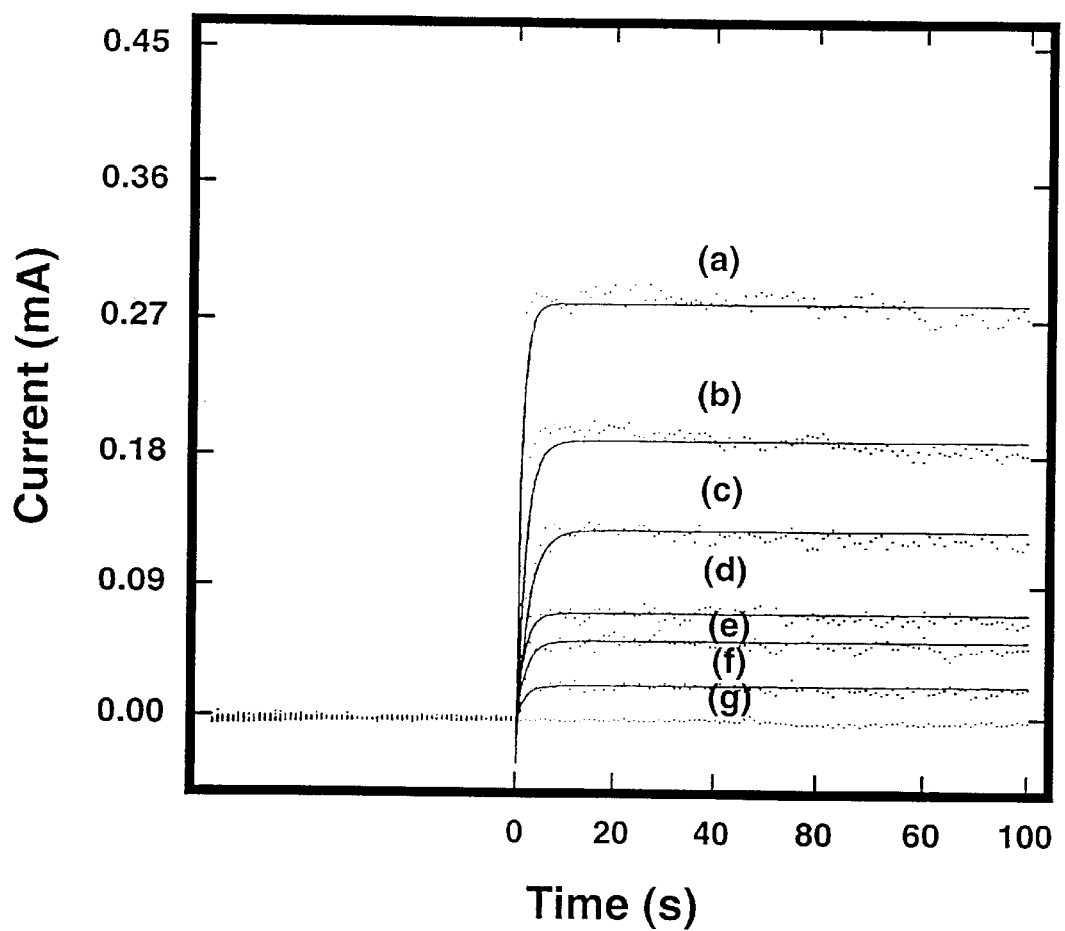

FIG. 12. Amperometric response cure showing response of three component sensor to varying concentrations of o-NPA.

Figure 13:
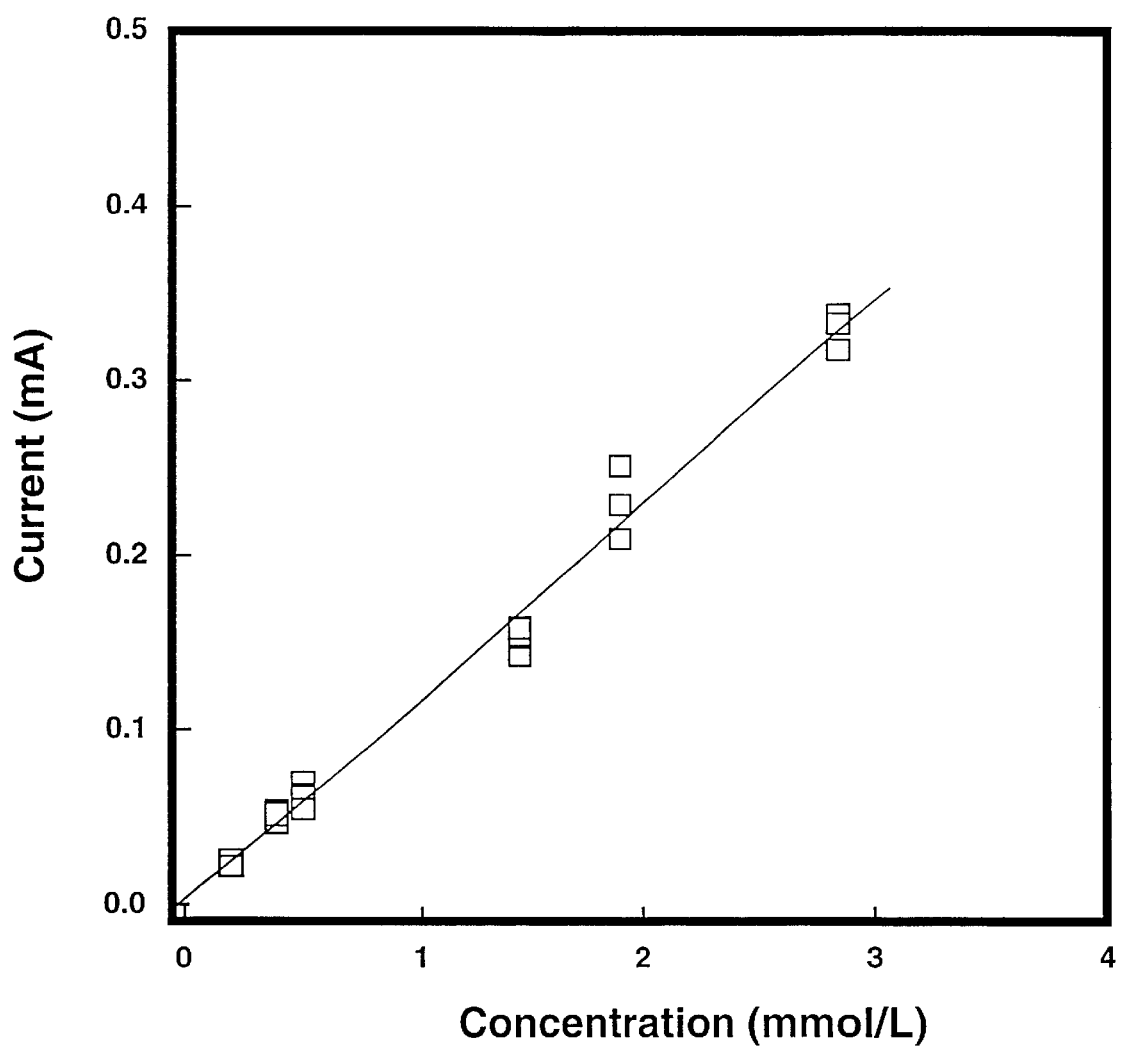

FIG. 13. Calibration curve plotting the data of FIG. 12.

Figure 14:
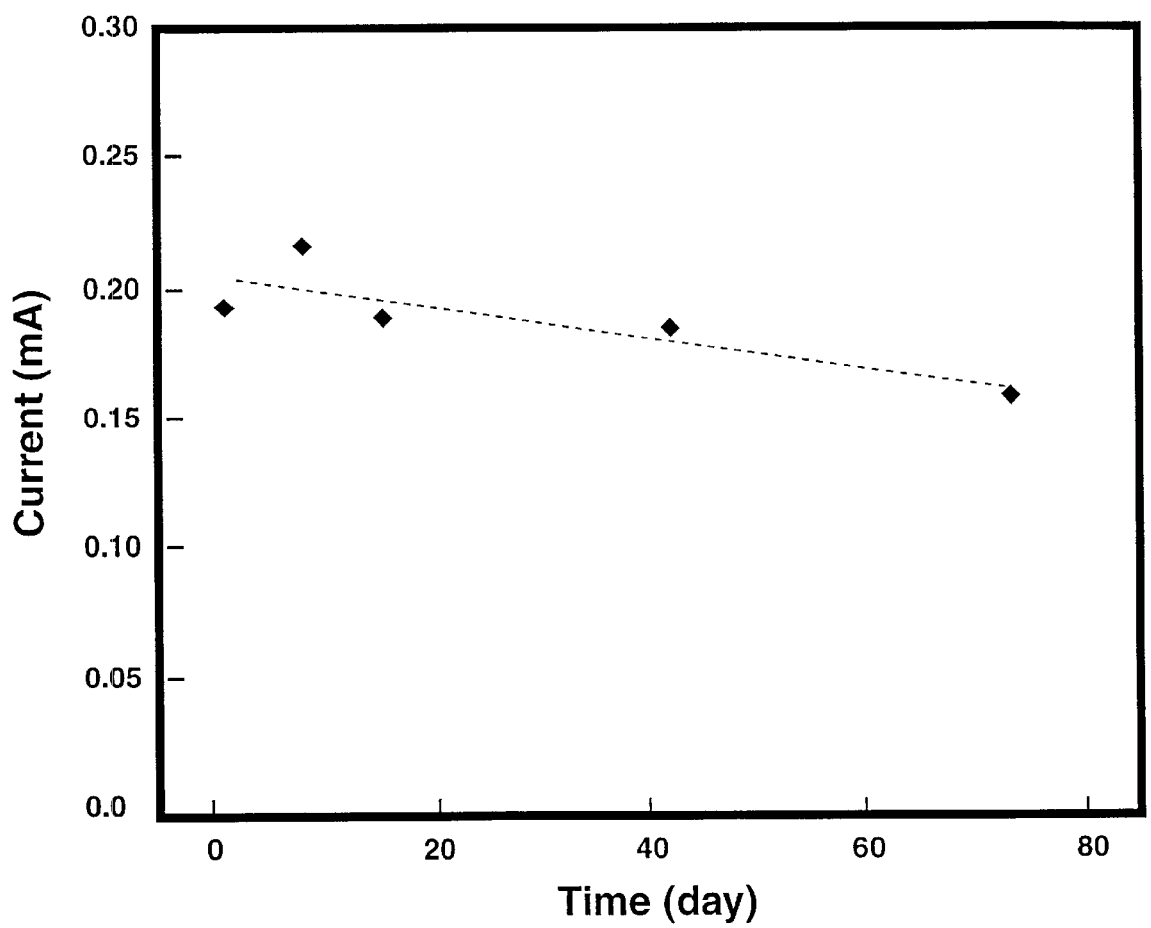

FIG. 14. Graph showing the operational stability of the present invention as a function of time.

DETAILED DESCRIPTION OF THE INVENTION

EXAMPLE 1

Construction of the Biosensor

The mM-β-DMCD as a biomimetic enzyme was synthesized as described earlier (Chen et al. 1993; Ikeda et al. 1989; Chen, E. T. unpublished cytotoxicity report of the mM-β-DMCD). Briefly, β-DMCD may be reacted first with sodium hydride in dry tetrahydrofuran under a nitrogen atmosphere at 35–38° C. for 10 hours. The solution is then cooled to 0° C. and mixed with a solution of 2-(4-imidazolyl)-ethyl bromide in tetrahydrofuran and heated to 25° C. for 10 hours to produce the mono-imidazolyl CD and 20 hours to produce the bis-imidazolyl CD. The reagents used were prepared as follows. Polyethylene glycol diglycidyl ether (PEG, MW 400, Polyscience Inc, PA 18976) was used as received. The poly(4-vinylpyridine) (PVP) (MW 50,000, Polyscience Inc, PA 18976) was purified before use by dissolving PVP into methanol and adding ether for precipitation. The precipitate was rinsed and dried. Acetonitrile was freshly distilled. o-NPA and p-NPA (Aldrich) were re-crystallized from hexane. m-NPA was synthesized according to a published method (Spasov 1939) and the purity was tested by using gas chromatography. All analyte solutions were prepared in acetonitrile and stored at 4.0° C. for 24 h before use. The aqueous buffer solutions at 0.067 mol/L concentration were prepared with various pH values for the pH dependence study. The electrolyte, potassium chloride, was used in the buffer solutions at 0.1 M KCl concentration. All solutions were prepared in deionized water that had been previously distilled (Corning megapure distillation apparatus, Corning Inc., Corning, N.Y.) and filtered through 0.2 μm pore size membrane filter (Nylon-66, Rainin Instrument Co., Inc., Woburn, Mass.). Sodium 4-(2-hydroxyethyl)-1-piperazineethanesulfonate (HEPES, Aldrich) was used as received. A solution of mM-β-DMCD (2g/L) was prepared in THF, and the PEG was prepared in water (2.3 g/L). A 0.4 mg/mL PVP solution was prepared in a 50:50 (v/v) mixture of methanol and HEPES at pH 8.2.

The various ingredients may be prepared as a solution in any suitable solvent in which they are soluble. The concentrations of the solutions may be varied without affecting the practice of the present invention. The cyclodextrin solution may be from about 2 to about 4 mg/mL; the PVP solution may be from about 0.4 to about 4 mg/mL and the PEG solution may be from about 2 to about 3 mg/mL. These three solutions of PVP, PEG, and mM-β-DMCD may be mixed in various proportions to generate the three component sensor coating of the present invention. In preferred embodiments the mixture may contain from about 3 to about 8 parts PVP solution, from about 2 to about 4 parts PEG solution and from about 8 parts to about 12 parts cyclodextrin solution. In a most preferred embodiment, the solutions may be mixed in the ratio of 5:2:10 (v/v) and this ratio was tested in sensor 1. A two component sensor coating may be constructed by omitting the PVP solution. In preferred embodiments the mixture may contain from about 2 to about 3 parts PEG solution and from about 7 parts to about 8 parts cyclodextrin solution. In a most preferred embodiment, the two component sensor may be made using a 30/70 ratio of PEG/mM-β-DMCD and this ratio was used for sensor 2. Capped containers with two- or three-component solutions were deoxygenated.

Preparation of the Biosensor

In a preferred embodiment, the reactor/sensor device may comprise mM-β-DMCD cross-linked with PEG and PVP (for sensor 1), or mM-β-DMCD cross-linked with PEG (for sensor 2) coated onto the surface of a glassy-carbon (GC) electrode (3 mm diameter, Bioanalytical System, West Lafayette, Ind. 47906). In other embodiments, the electrode may be made of any material known to those skilled in the art for the construction of electrodes. In other preferred embodiments, the electrode may be constructed of gold, silver, platinum or other metals.

Those skilled in the art will appreciate that the following description of construction of the biosensor of the present invention employs a glassy carbon electrode and can be readily adapted to construction of sensors using other electrode materials. Prior to coating, the GC electrode was polished using alumina and then rinsed and placed in a sonicating water bath for several minutes. Then the electrode was rinsed thoroughly with twice distilled water before use. A 2 μL aliquot of mixed solution was coated onto the surface of the electrode. After coating, the sensor was put in an oven for 48 h at 37.0° C. After drying, the coated electrode was rinsed with twice distilled water for 10 minutes and dried in an oven for 2 h. The surface morphology of the BMZ sensor was imaged by STM (Nanoscope II, Digital Instrument), and SEM (JSM-35C, JEOL LTD, Japan). A microwave vacuum plasma cleaner was used to clean the substrate surface (Opthos Instrument, Md.). For the STM experiments, a 1×1 cm² gold (111) crystal film was cleaned by a microwave vacuum plasma cleaner, was dipped into prepared solutions for a day, was dried in the oven for 2 h, and was then ready for the STM image. For the SEM experiment, a gold (111) film of 2×1.5 cm² was immersed into a two-component mixture solution, then the procedures were followed as above.

Instrumentation

The BMZ sensors were characterized using a cyclic voltammetry (CV-27, Bioanalytical System Inc., West Lafayette, Ind. 47906). Time-dependent responses for the amperometric method were recorded with the same equipment under the amperometric mode with a controlled constant polarizing potential. The output signal was digitized (Lab Master, Scientific Products, Cleveland, Ohio 44139) and stored on-line with a computer (Gateway 2000) with a math coprocessor. The glassy carbon (GC) electrode was the working electrode. The reference electrode was silver/silver-chloride and the auxiliary electrode was Pt.

Amperometric Measurements

All measurements were made on 20.0 mL solutions kept at 25.0° C. (except the temperature effect study) in a water-jacketed, single-compartment electrochemical cell. Test solutions were covered all times by a stream of nitrogen that had passed through a saturated solution of sodium sulfite to remove oxygen. A polarizing potential of −0.80 V was applied, and when the Faradic current decayed to a steady-state (s-s) value, the analyte (1.0 mL) was injected. Signal acquisition (1 point/s) began when the background current reached steady-state. The stirring rate was held constant using a NUOVA II stirrer (Barnstead Thermolyne Inc., Dubuque, Iowa).

Cyclic Voltammetric (CV) Measurements

For the CV measurement, the potential sweep range may be set from −0.8 V to 0.8 V. The scan rate was set at 20 mV/s for all experiments. The concentration of NPA isomers were 0.20 mmol/L in carbonate buffer at 9.87, 25.0° C. for the molecular recognition study. Those skilled in the art will appreciate that the experimental parameters may be adjusted to optimize the results obtained for various analytes and biosensors. For example, when the electrode is constructed of silver, the scan range may be adjusted to −0.8 to 0 V to avoid oxidation of the silver electrode at higher positive potentials.

EXAMPLE 2

BMZ Nanotube Device

Figure 1:
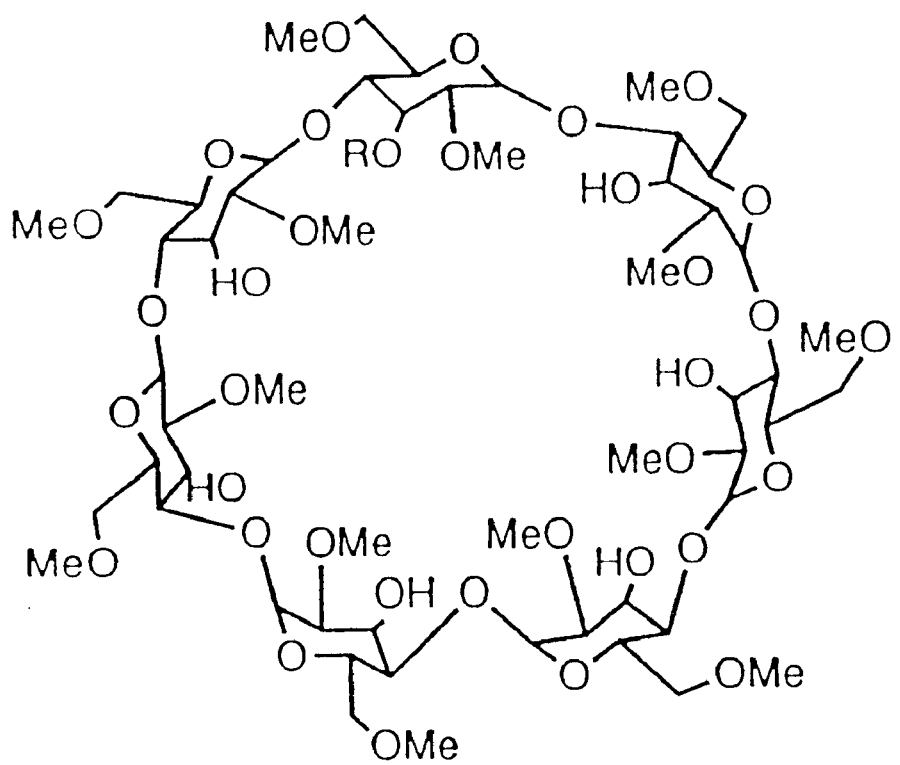
FIG. 1. A representation of the structure of a catalytically active cyclodextrin.
Figure 1:
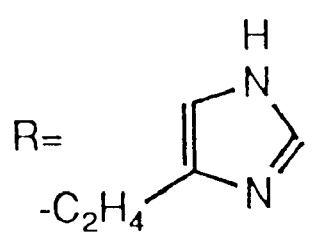
Figure 2:
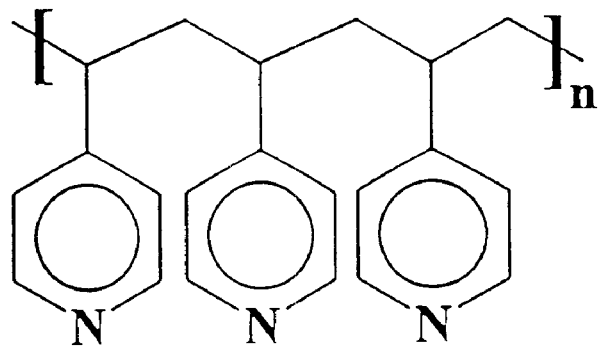
FIG. 2. A representation of the structure of PVP.
Figure 3:
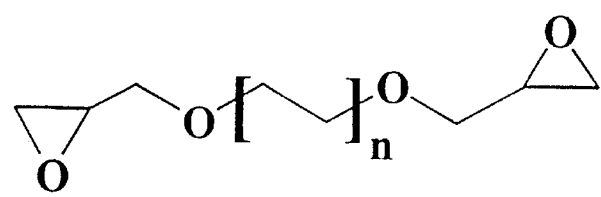
FIG. 3. A representation of the structure of PEG.
Figure 4:
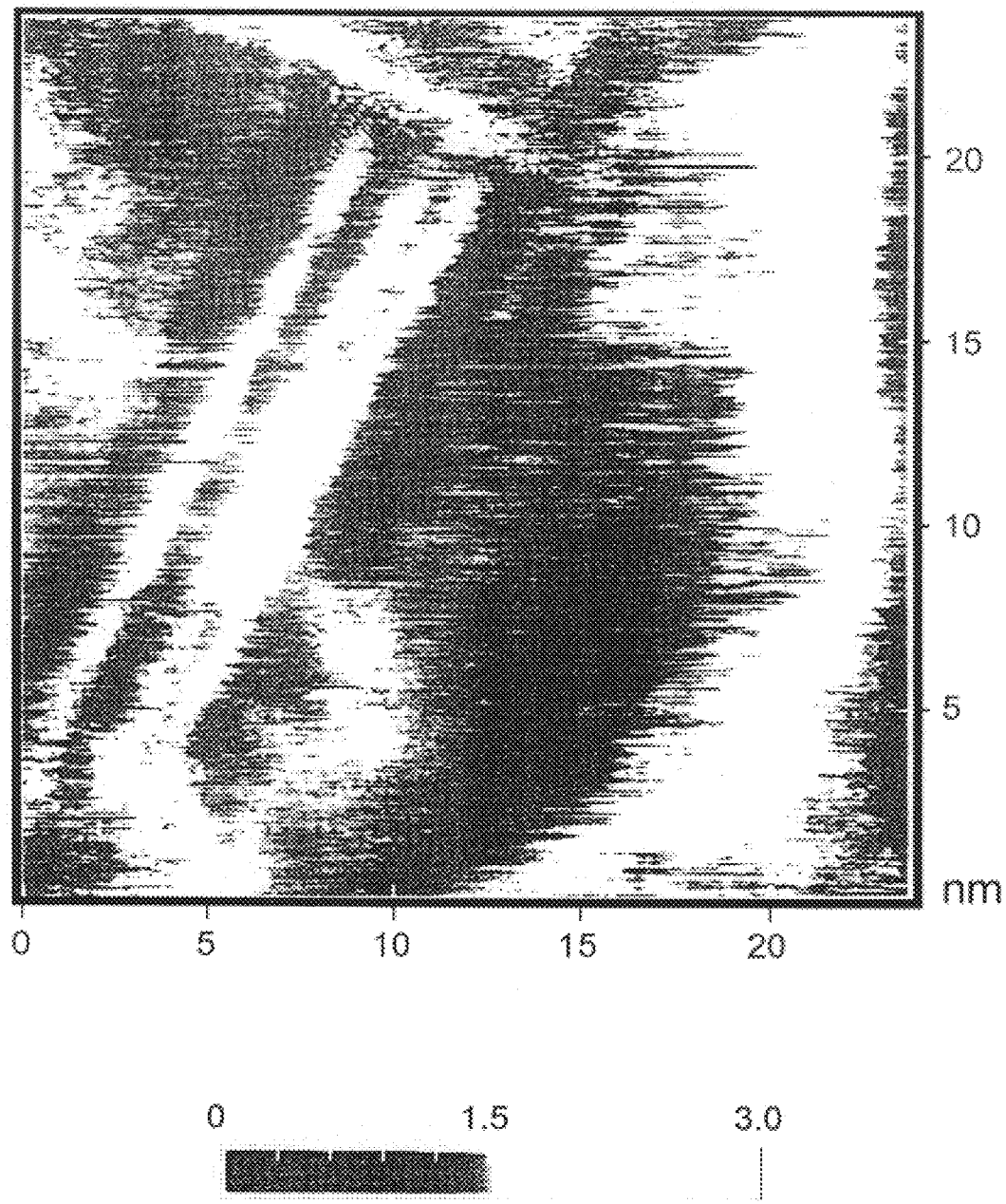
FIG. 4. A micrograph obtained by Scanning Tunneling Microscopy (STM) of the surface of gold substrate coated with mM-β-DMCD in the presence of PVP and PEG.

FIGS. 1–3 show the structures of mM-β-DMCD, PVP and PEG used for fabrication of the biomimetic sensors. Sensor 1 is constructed using all three components and sensor 2 is constructed with only two components as PVP is omitted. The nanotube structures from self-assembly of mM-β-DMCD-PVP-PEG (sensor 1) on the surface of a gold (111) crystal planar electrode as imaged by STM are shown in FIG. 4. The structure of the molecular nanotube of mM-β-DMCD linked by PVP and PEG was imaged by a Scanning Tunneling Microscope (STM) on a gold (111) crystal film at setpoint 11.0 nA with 199.9 mV bias. The average length and width of the three nanotubes visible in FIG. 4 are 26.2±1.0 nm and 2.5 nm, respectively. The packing density of the nanotubes on the crystal gold (111) planar electrode, as revealed by STM images, influences sensor performance as discussed later.

Figure 5:
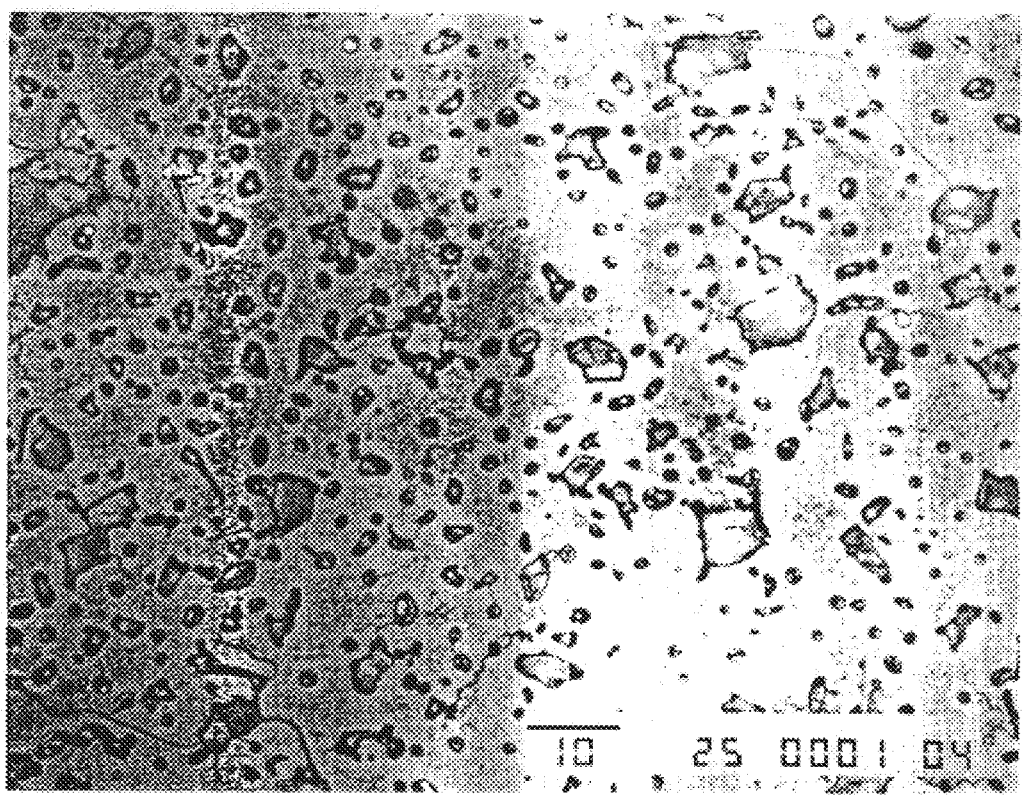
FIG. 5. A micrograph obtained by Scanning Electron Microscopy (SEM) of the surface of gold substrate coated with mM-β-DMCD in the presence of PEG.

FIG. 5 is a Scanning Electronic Microscopy (SEM) image of the surface of mM-β-DMCD linked by PEG on a crystal gold (111) substrate (2×1.5 cm²) by a spontaneously adsorbed method.

In FIG. 5, the SEM image of sensor 2 shows the two component coating forms a polycrystalline film on the surface of a gold (111) planar electrode.

Figure 6:
FIG. 6. A micrograph obtained by Scanning Electron Microscopy (SEM) of the surface of gold substrate coated with mM-β-DMCD in the presence of PVP and PEG.

FIG. 6 is an SEM image of the surface of mM-β-DMCD linked by PEG and PVP on a crystal gold (111) substrate. FIG. 6 shows that the three component system forms nanotube structures. Tubules with varying length were observed on the crystal gold (111) planar surface. Comparing the two physical structures produced by the two different formulations used to make the sensors reveals that the formulation used to make sensor 1 produces a nanotube structure while the formulation used to produce sensor two results in a polycrystalline coating. From this comparison is seems reasonable to conclude that PVP is necessary for the formation of nanotubes with mM-β-DMCD. Perhaps the guest-host interaction between PVP and mM-β-DMCD promotes aligning of the CD cone to form nanotubes.

In making a comparison of the STM image of FIG. 4 to the SEM image of FIG. 6 it should be borne in mind that both films were made using the by three component formulation. The only difference is the proportion of each of the components within the formulation. Solutions of 0.4 mg/mL PVP, 2.3 mg/mL PEG and 2 mg/mL cyclodextrin were prepared as described above. For the STM image these solutions were mixed in a 5:2:10 (v/v) ratio and for the SEM image the solutions were mixed in a 3:2:12 (v/v) ratio.

The STM image reveals a denser packing of the nanotubes than that of the SEM in FIG. 6. Thus, the density of packing of the nanotube structure can be controlled by varying the proportions of the components. The same effect was seen in the two component system.

Several different proportions were tried for the for two-component system, but none had tube structure imaged by SEM. However, after adding PVP to the two-component solution, nanotubes were formed regardless of changing the proportion.

EXAMPLE 3

Molecular Recognition

Cyclic voltammetry (CV) was used to study the unique features of the BMZ sensors and to evaluate feasibility in a preliminary study. The study revealed that mM-β-DMCD enhances current from NPA even in presence of $NPO^-$ in a homogenous buffer solution. In an expanded study, BMZ sensors were constructed by using PEG and mM-β-DMCD to coat gold, silver and GC electrodes.

The coated electrodes were used to obtain CV voltammograms and the results were compared with one another.

The various electrode materials resulted in the production of BMZ sensors having differing response characteristics. The differences between the BMZ/GC, BMZ/gold and BMZ/silver sensors are (1) the BMZ/GC sensor has fast response time, (2) the BMZ/gold sensor and BMZ/silver sensor provided oxidation-reduction peaks within the scan range from –0.8 to 0.8 V, and the peaks showed a degree of irreversibility. In contrast, the BMZ/GC electrode showed only one intense reduction peak that was predominately irreversible. The degree of molecular recognition of o-NPA among other isomers for the three BMZ sensors were in the order of GC>silver>gold. Therefore, GC electrodes were used for a detailed analysis of the ability of the BMZ electrodes to distinguish among the three isomers of NPA. There was no significant peak change in the CV profiles of o-NPA using the bare electrode through consecutive scans. The m-NPA and p-NPA have CV profiles similar to that of o-NPA. This indicates that the bare electrode has no molecular recognition, nor differences in catalytic behaviors toward the three structural isomers.

Figure 7:
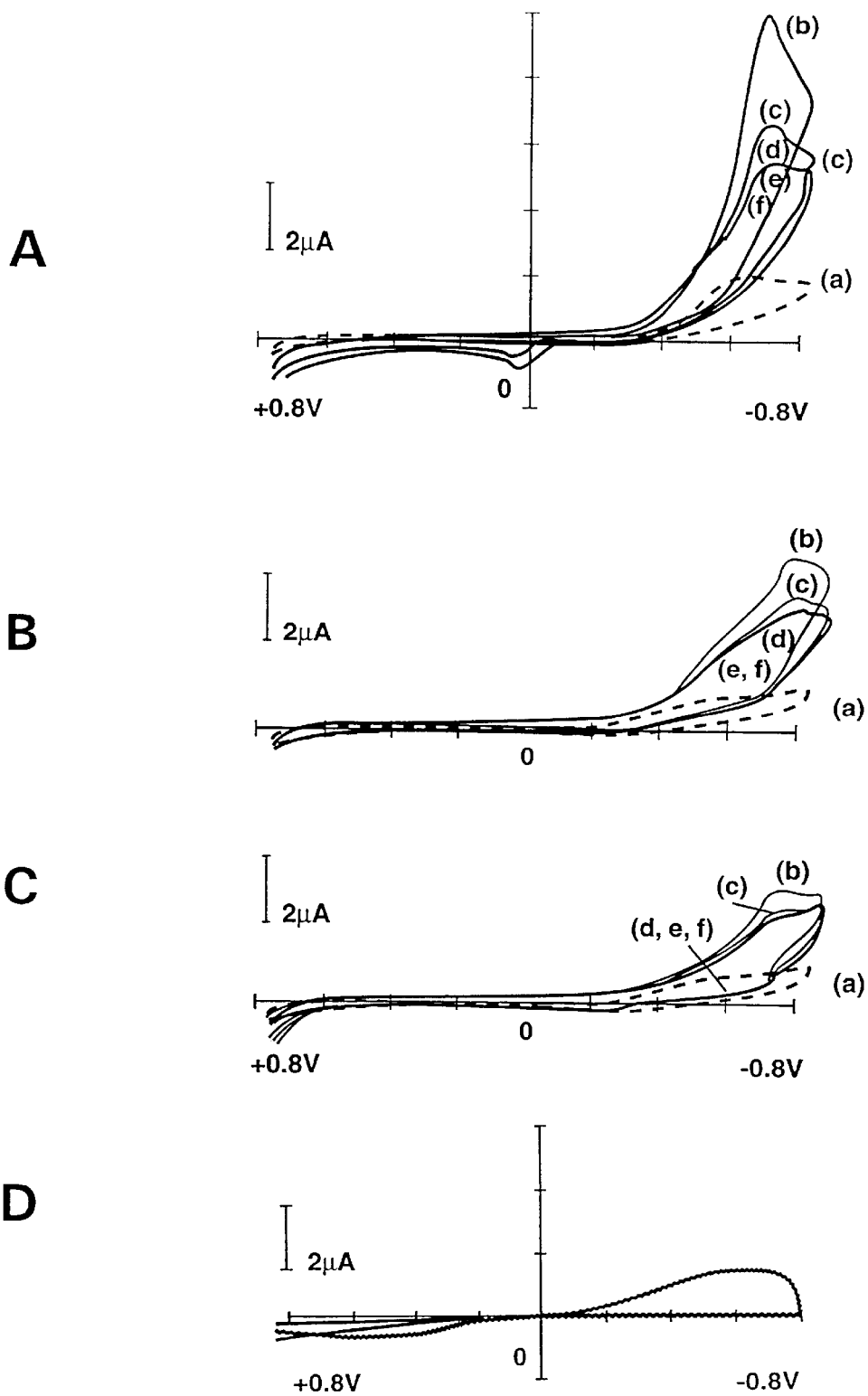
FIG. 7. Cyclic voltammogram obtained with the sensor of the present invention.

Initially, consecutive CV scans were applied to two BMZ/GC sensors, sensor 1 with three-component fabrication, and sensor 2 with two-component fabrication, in order to: (1) find whether or not there is a positive correlation between the cathodic currents and time, (2) find the right polarizing potential to measure the cathodic current (3) find the appropriate data acquisition rate for an amperometric method. An attempt was made to find the steady-state current. Cyclic voltammograms were obtained using the BMZ sensor in order to test for the molecular recognition of the various isomers of NPA. The tests were conducted in pH 9.87, 0.067 mol/L buffer solution with 0.10 M KCl at 25.0° C. FIG. 7 shows the results obtained with a glassy carbon (GC) electrode fabricated with mM-β-DMCD, PEG and PVP. Panel A shows the results obtained without (dotted curve a) and with $2.0 \times 10^{-4}$ mol/L o-NPA. The solid curves b-f were with o-NPA in consecutive scans (scan rate 20 mV/s). Panel B shows the results obtained without (dotted curve a) and with $2.0 \times 10^{-4}$ mol/L p-NPA. The solid curves b-f were obtained in consecutive scans as above. Panel C shows the results obtained without (dotted curve a) and with $2.0 \times 10^{-4}$ mol/L m-NPA $2.0 \times 10^{-4}$ mol/L. The solid curves b-f were from consecutive scans as above. The reference electrode is Ag/AgCl, and Pt is the auxiliary electrode. Panel D shows the results obtained with the bare electrode and o-NPA. Under identical experimental conditions, the BMZ sensor 1 responses to o-NPA were enhanced (FIG. 7) by comparison with the bare electrode.

The o-NPA has the highest catalytic peak as shown in FIG. 7. The CVs for all three isomers show the current decreases as the number of consecutive CV scans increase. By plotting the peak current vs CV scan from 80 to 640 s (1–8 scans), a negative correlation for each of the three isomers was found between peak current and the elapsed time. Those skilled in the art appreciate that it is common for the initial CV scans to be different from subsequence scans and these are often ignored in analytical determinations. Scans 3–5 appear to represent a steady-state response with CV. An exponential decay curve was observed for each isomer, data is not shown.

These observations suggested (1) the sensor has very fast response time and the peak limiting current at steady-state may not be seen at the scan rate used. (2) It is appropriate to use an amperometric method to evaluate the performance of the BMZ sensors quantitatively. A well-defined catalytic reduction peak for the o-NPA is obtained at –0.68 V as shown in FIG. 7. From FIG. 7, we can conclude that this sensor indeed selectively favors the o-NPA rather than meta and para isomers. The special recognition for ortho isomer also confirmed with other BMZ electrodes described earlier in this section. Sensors prepared with two components showed a similar trend for molecular recognition.

By comparison with sensor 2 shown in FIG. 8, it is clear, that sensor 1 has drastically reduced the background current by 2.5-fold. FIG. 8 shows a cyclic voltammogram with and without $2.0 \times 10^{-4}$ mol/L o-NPA in 0.067 mol/L, pH 9.87 buffer with 0.10 M KCl at 25.0° C. The GC electrode was fabricated with mM-β-DMCD and PEG only. The dotted curve is for blank as (a). The solid curves are with o-NPA using consecutive scans as (b-g). The scan rate was 20 mV/s. Comparison of FIGS. 7 and 8 reveals that sensor 1 produces 30% more peak current than produced by sensor 2. This observation has been confirmed amperometrically.

The sensors successfully demonstrate well-defined, single electrocatalytic peaks for the three isomers. The sensors do not oxidize the hydrolysis product $NPO^-$ within the scan range employed, so the problem of fouling of the electrode can be avoided. Sensor 1 has good coverage of $3 \times 10^{19}$ molecule/cm$^2$, based on the equation of $\Gamma = Q/nFA$, $\Gamma$ is the surface coverage, Q is the charge, n is the number of electrons, F is the Faraday constant and the A is the sensor conducting area. By subtracting the charge from the bare electrode response to the analyte, the net charge will be the contribution from the electrocatalytic reaction.

Since a well-defined electrocatalytic peak was obtained and the applied potential is also known, it is advantageous to make amperometric measurements. Plots of current vs. time for the three isomers using either sensor 1 or 2 confirms that the magnitude of the amperometric current among the three isomers is in the order of o-NPA>m-NPA>p-NPA, but the order is reversed for the rate constants.

Both sensors are capable of detecting o-NPA, based on their well-defined catalytic reduction currents sensor 1 being somewhat more effective than sensor 2. PVP enhanced the biosensor performance perhaps by permitting the formation of nanotube structures. The novelty of this fabrication technology is to form a firm smooth co-polymer network of catalytically active cyclodextrin cross-linked with PVP through the PEG. This unique approach minimizes formation of pin-holes in the membrane.

The three component system acts as an electron barrier to o-NPO$^-$ as shown in FIG. 9 which shows a cyclic voltammogram with and without $4.80\times10^{-4}$ mol/L o-NPO$^-$ in 0.067 mol/L, pH 9.87 buffer with 0.10 M KCl at 25.0° C. The GC electrode was fabricated with mM-β-DMCD and PEG and PVP. The bare GC electrode responses to o-NPO$^-$ is shown by the dotted curve, and the BMZ/GC electrode responses to o-NPO$^-$ with the solid curve. The immobilized three-component monolayer has suppressed the permeation of the o-NPO$^-$ ions to the electrode. The suppressed peak is more irreversible than that of bare electrode, and the background current has been remarkably reduced by the membrane. This observation is consistent with the literature (Chung 1990).

EXAMPLE 4
Supramolecular Channel Amplification

Supramolecular channel devices were defined as structurally organized and functionally integrated chemical systems built into supramolecular architectures by Jean-Marie Lehn (Lehn 1985). Current progress in the construction and characterization of supramolecular devices has been reported (*Proceedings of the NATO Advanced Research Workshop on Chemosensors of Ion and Molecular Recognition*, Kluwer Academic Publishers, Bonas, France, 1997; Editors Scheller, F. W., Schubert, F., Fedrowitz, J., *Frontiers in Bosensorics*, books one and two, Birkh-user Verlag Base, Boston, 1997; Szejtli et al. 1996). Molecular recognition and amplification are the two distinguishing features of supramolecular channel devices. Evaluation of the amplification effect of the new developed BMZ sensor is done based on evaluation of the signal to noise ratio (S/N), and the rate constants of the electrochemical reactions.

As shown in FIG. 4, the three component coating of the present invention spontaneously forms nanotube structures. Amperometric response curves are shown in FIGS. 10 and 11. These figures show amperometric time-dependent response curves with and without surface immobilization at pH 7.20, 0.067 mol/L buffer with 0.10 M KCl, 25.0° C. In FIG. 10, (a) represents the response curve of the BMZ/GC sensor 1 (i.e., mM-β-DMCD+PEG+PVP) to 0.48 mmol/L of o-NPA in pH 7.2 solution, (b) represents the sensor 1 response curve to 0.48 mmol/L of o-NPO$^-$, and (c) is the bare electrode responses to 0.48 mmol/L of o-NPO$^-$. In FIG. 11, (a) and (c) are the same as (a) and (c) of FIG. 10, and (b) is the bare GC electrode response to o-NPA. These figures clearly illustrate that the bare electrode produces high noise and weak signal. In contract, the BMZ sensor has 30-fold increase in the S/N ratio by comparison with bare electrode as illustrated in FIG. 10 between (a) and (c). This demonstrates the ability of the BMZ sensor to enhance the signal and reduce the noise based upon its electrocatalysis. Comparing (a) and (b) in FIG. 10, the BMZ sensor of the present invention responds to o-NPA and o-NPO$^-$ very differently, even under same conditions. This is also seen by comparison of the CV voltammograms of the BMZ sensor 1 response to o-NPA in FIG. 7 to the response of the sensor to o-NPO$^-$ as shown in FIG. 9. The responses to o-NPA and o-NPO$^-$ were totally different. We are unable to explain the drastically different responses in terms of electrochemical mechanisms explicitly without further experiments.

An experiment was conducted by simultaneously measuring UV absorbance of NPO$^-$ and amperometric current under an applied potential using sensor 1. Here sensor 1 serves as an electro-optical sensor. The colorless solutions very quickly changed to yellowish color after injecting the NPA analyte or phenyl acetate. The UV absorbance of NPO$^-$ is enhanced, as is the initial rate of formation of NPO$^-$, as measured as the change of absorbance vs time, compared with a GC bare electrode. This indicates that hydrolysis of the ester occurred, and mM-β-DMCD catalyzed the hydrolysis reactions heterogeneously. This demonstrates that sensor 1 may be used as an electro-optical probe.

Without wishing to be bound by the theory, it is hypothesized that the nanotubes with more than 20 CDs lay on the surface of the electrode and become an organic electronic conductor. The organic electron conductor serves to transfer electrons to the electrode surface when the catalysis reaction occurs. Recently, Dagani reported in C&EN about the electronic applications of carbon nanotubes (Dagani 1998). Formation of nanotubes can lead to a major changes in the electronic properties of CDs allowing them to serve as microelectronic devices. The nanotubes functioning as electronic channels promoting electron flow may explain why the response time is so fast. The first-order rate constants for the electrocatalytic reaction are 0.31 s$^{-1}$ and 0.19 s$^{-1}$ for sensor 1 and sensor 2 at pH 9.87, 25.0° C., respectively. This evidence clearly demonstrated that the sensor 1 has supramolecular channel amplification effect, that sensor 1 not only improved the sensitivity by 31% compared with sensor 2 described in next section, but also improved the rate constant. Perhaps the nanotube packing facilities the electron transfer, hence overall rate is increased. In contrast, sensor 2 does not have PVP, therefore nanotube structure is not likely, because PEG does not contain an aromatic ring and lacks hydrophobicity. According to Li's report, a compound with an aromatic ring is necessary to form nanotubes with CDs (Li et al., *Science* 1994).

In the absence of catalytic effects, the BMZ sensor only improves the S/N ratio by 4.7 times and slightly improves the signal intensity for o-NPO$^{31}$. This is seen by comparing the response of the BMZ sensor to o-NPO$^-$ ((b) in FIG. 10) to the response of the bare electrode to o-NPO$^-$ ((c) in FIG. 10). The bare electrode can detect o-NPA with a very small S/N ratio, as shown in FIG. 11 (*b*).

EXAMPLE 5
Response Curves

FIG. 12 illustrates a typical set of time dependent amperometric response curves for measuring o-NPA with sensor 1 fabricated with three components. The data was obtained at different concentrations of o-NPA in pH 9.87 buffer solution with 0.10 M KCl, at 25.0° C. The concentrations were as follows from a to g: o-NPA(mmol/L) 2.86, 1.90, 1.43, 0.48, 0.38, 0.19, 0.00. Experimental data( . . . ), Fitted data (—).

All response curves approach steady-state monotonically. The dotted curves are the experimental data, and the solid curves are the fitted data by using a predictive curve fitting method to fit a first-order model to 0–40 s data. The predictive curve fitting method is to fit a suitable mathematical model to the transient data and then to predict the steady-state signal, if the signal reaches a steady-state (Chen et al. 1993; Pardue 1989; Williams et al. 1996; Lim et al. 1996; Wang et al. 1997). The pseudo first-order rate constants for the approach to steady state at different concentrations were constant at 0.31/s, this strongly suggests that the sensor's fast responses are not concentration dependent. This is truly an advantage for practical applications, and also overcomes the drawbacks of the response time depending on the analyte concentration as for an amperometric phenolic sensor made with the natural enzyme (Kotte et al. 1995).

EXAMPLE 6

Sensitivity

As shown above, utilizing the catalysis of modified CD and self-assembly of three-component fabrication enabled the detection of NPA esters in a more convenient way than those methods of the prior art. An important distinction between the present invention and those methods and devices of the prior art is that the present invention does not require a mediator molecule. As a result, no loss of signal due to the inefficiency of the coupling reaction is seen. In addition, the bioselectivity of catalytically active cyclodextrins overcomes the interference between isomers. Finally, the response of the present invention is rapid compared to those methods of the prior art; the half-life for the electrochemical detection is 2 s.

The sensor of the present invention has a linear response over the range tested. FIG. 13 shows the calibration plot of the measured amperometric current vs. concentrations of o-NPA for the BMZ sensor 1. FIG. 13 demonstrates that the sensor has good linearity for sensor 1.

The sensitivity results for comparing with two sensors were shown at first column of slope in Table 1.

TABLE I

Least-squares statistics for measured current vs. concentrations of o-NPA for BMZ sensors with different fabrications[a]

| Slope[b] ($\mu$A/mmol/L) | | Intercept (mmol/L) | | Std. Error of Estimate (mmol/L) | Correlation Coefficient (r) | Pooled Std. Dev.[c] (mmol/L) |
|---|---|---|---|---|---|---|
| Value | Std. Dev. | Value | Std. Dev. | | | |
| (Sensor I[d]) | | | | | | |
| 102.1 | 2.83 | 0.078 | 0.043 | 0.113 | 0.9970 | 0.0953 |
| (Sensor II[e]) | | | | | | |
| 78.0 | 3.90 | 0.147 | 0.049 | 0.130 | 0.9915 | 0.1295 |

[a]the unit for intercept, standard error of estimate and poled standard deviation was expressed in mmol/L, based on the values of each item divided by the value of slope, in order to facilitate the comparison.
[b]refers to the sensitivity on a total area of 0.07 $cm^2$ BMZ electrode.
[c]Three replicate runs on each of six concentrations in the linear range of 0.190 to 2.86 mmol/L for sensor 1. The currents are within 24.5 to 350 $\mu$A. Three replicate runs on each of five concentrations in the linear range of 0.0952 to 1.90 mmol/L for sensor 2. The currents are within 15.5 to 170 $\mu$A. Both sensors averaged 30 points of the steady-state current from 30 to 60 seconds. The reactions were monitored for 0 to 200s.
[d]Uses three-component fabricaton of the BMZ sensor.
[e]Uses two-component fabricaton of the BMZ sensor.

The slope shows the sensitivity for measured current vs. concentrations at a 0.07 $cm^2$ BMZ/GC electrode. The sensitivity has increased from 1.11±0.04 A L/mol $cm^2$ (78 $\mu$A/mmol/L/0.07 $cm^2$) for the sensor 2 to 1.46±0.04 A L/mol $cm^2$ (102.1 $\mu$A/mmol/L/0.07 $cm^2$) for the sensor 1. The 31% increase in sensitivity confirms the advantage of using the three-component fabrication technique with the nanotube arrangement. This novel BMZ sensor also demonstrates an increasing sensitivity by 4 to 6 fold compared with Kotte's (Kotte et al. 1995) sensors, and 14-fold compared with Luong's glucose sensor (Zhao et al. 1993). A 280-fold enhanced sensitivity compared with Liu's glucose amperometric sensor made with cyclodextrin polymer (Liu et al. 1998).

The two BMZ sensors demonstrate the capability to detect o-NPA in a linear range from 0.0952 to 1.90 mmol/L for sensor 2, from 0.19 to 2.86 mmol/L for sensor 1. Sensor 1 has negligible systematic error as shown by the negligible intercept in Table 1, the intercept for sensor 2 was not negligible according to a 2-tail t-test at 95% confidence level with P<0.001.

Imprecision

Biosensors, especially BMZ sensors, often suffer low precision. There are very few, if any, attempts in the prior art to create a highly reproducible BMZ sensor (Bucke et al 1998). The prior art recognizes that many difficulties are encountered during the development of BMZ biosensors. Likewise, the development of CD-based sensors that possess bio-recognition and reproducibility has been an equally unattainable goal. The present invention has achieved unexpectedly precise results as shown by the data in Table 1. The last column in Table 1 included the pooled standard deviations for the sensors for three replicates at each of six, and five concentrations, for sensor 1 and 2, respectively. The pooled standard deviations were 95.3 $\mu$mol/L (n=18), and 129.5 $\mu$mol/L (n=15), corresponding to relative standard deviations of 5.6 and 9.9% for signals at average concentrations for sensor 1 and 2, respectively.

Stability

The stability of the steady-state currents measured by the BMZ sensor was not dependent on analyte concentrations as shown in FIG. 12. In other words, when the current reaches a steady-state, its magnitude remained constant regardless of the analyte concentration used. This demonstrated the utility of the sensors. The operational stability has been investigated by using the amperometric method to measure o-NPA at 1.92 mmol/L concentration at pH 7.2, 25.0° C. for a period of 2.5 months and the results are shown in FIG. 14. Sensor 1 was quite stable under the operating conditions tested. The signal intensity had no significant drift, only 0.2%/day drift over 42 days, while the sensor has performed 68 measurements with different assays over that period. After 42 days, the rate of the signal drift increased slightly to 0.58 $\mu$A/day. Overall, the signal decreases less than 0.3%/day compared to the initial signal. Over 2.5 months, sensor 1 made 96 measurements with only a 17.7% loss in signal, and 10.7% loss in signal after two months with 80 measurements. By way of comparison to BMZ sensors of the prior art, Liu's sensor lost 14% of its original activity while in storage for: two months. It should be noted that the sensor did not make measurements during this period (Liu et al. 1999). The operational stability of the BMZ sensor is superior to the sensor made with natural enzyme that lost 30.8% of its initial response after 96 assays (Wang et al. 1997). Thus, the sensor of the present invention is unexpectedly superior instability to those of the prior art.

Effect of pH

The pH effects on first-order rate constant were determined and the response currents were included in Table 2.

TABLE II

The pH effects on the measurement objectives based on the amperometric biomimetic sensor

| pH | 9.87 | 8.20 | 7.20 | 6.50 | RSD (%) |
|---|---|---|---|---|---|
| | Value (Std. Dev.) | | | | |
| $I_x$ (mA) | 0.31(0.02) | 0.33(0.08) | 0.36(0.03) | 0.34(0.01) | 6.1 |
| $k_p$ $s^{-1}$ | 0.31(0.02) | 0.30(0.02) | 0.30(0.04) | 0.29(0.02) | 2.7 |

$I_x$ was obtained by an average of 30 points of the steady-state cathodic current.
$k_p$ was obtained by using a predictive multiple curve fitting method to a first-order model. The data of the rate constant were for triplicate runs. The concentration of o-NPA was 2.86 mmol/L for rate constant and current measurement at 25.0° C. The buffer concentration was 0.067 mol/L with 0.10 M potassium chloride.

The second row is the steady-state current with different pH. The current has a relative standard deviation (RSD) of ±6% of the average current from the pH range 6.50 to 9.87 at 25.0° C. This is an obvious advantage of the biomimetic enzyme over the natural enzyme. The third row is for the first-order rate constants using a predictive curve fitting method averaged for triplicate runs. The pH has even less influence on the rate constants than the current, without consideration of the current effects, only a RSD value (%) of ±2.7% error related to the average rate constant. The total error, including current effects=±$(RSD^2_{current}+RSD^2_{rate})^{1/2}$ (Ross et al. 1998). This unexpected feature of insensitivity to pH enhances potential applications of BMZ sensor.

Effect of Temperature

The effect of temperature on the rate constant and current has been studied. A temperature decrease from 25.0° C. to 0.0° C. decreases the rate constants about ten times at pH 7.20 for isomers at 2.86 mmol/L concentration. This corresponds to a 0.011 $s^{-1}$/° C. decrease. This effect was similar for all three isomers. The steady-state current intensity was less effected by comparison with the effect of pH. Values of 1.2, 0.5 and 0.6%/° C. decrease in the signal intensity for o-, m- and p-NPA isomers from 25.0 to 0.0° C. has been observed. For natural enzymes, for example tyrosinase, when the temperature is lower than 10° C., the sensor becomes dysfunctional, because the enzyme activity decreases to less than 50% of the initial activity (Wang et al. 1997). Obviously, the BMZ sensor of the present invention has improved operational characteristics compared to the sensors of the prior art.

The sensor of the present invention has demonstrated a number of unexpected and unique features as compared to those sensors of the prior art. One feature of the present invention that is unique is the catalytic activity of the cyclodextrins used. This permits the construction of a sensor that does not require the presence of a mediator. In addition, only 2.3 ng of mM-β-DMCD is needed for fabrication of a BMZ/CD sensor. The sensor of the present invention provides specific molecular recognition of o-NPA over other structural isomers leading to reduced interference. The unique molecular structure of the present invention results in a sensor with a very fast response time that is not dependent on the analyte concentrations. This overcomes one of the major problems with the immobilized enzyme based sensors of the prior art. The BMZ sensor significantly improved the S/N by 30-fold compared with bare electrode and it acts as a molecular channel amplifier. The well-defined BMZ/CD sensor system has negligible systematic error. The sensors of the present invention are less affected by pH and temperature; hence, these features made them superior to sensors made with natural enzyme.

EXAMPLE 7

Applications of the Present Invention

The present invention will find use in the analysis of samples in order to detect the presence of toxic chemicals. The samples may be derived from any source including, but not limited to, environmental sources, such as bodies of water, soil samples and the like. When the samples are solid, an extraction process may be necessary to place the toxic materials in solution or suspension in order to facilitate their detection. The samples may be derived from industrial sources including but not limited to, waste streams, reagent streams, reactors and the like. The sensors of the present invention may used in an industrial setting to monitor the course or progress of a synthetic reaction. The present invention may be used to analyze samples derived from a clinical setting including, but not limited to body fluids and the like. In a preferred embodiment, the sensors of the present invention will be incorporated into a micro device to be used in flow systems and will enable detection of even lower levels of toxic chemicals. Such a portable micro-chip device may be used to detect low levels of toxic chemicals ingested by humans and animals, for example, aspirin and salicylic acid overdoses in children. The construction of such a micro device incorporating the sensors of the present invention is well within the ambit of ordinary skill in the art (Wang 1997; *Biosensors and Electronic Noses, Kres-Roger, Editor,* 1997).

The present invention has been described making use of certain, non-limiting examples. One skilled in the art can easily ascertain the essential characteristics of the present invention from these examples and, without deviating from the spirit and scope thereof, can make changes and modifications to adapt the invention to various uses and conditions. Such changes and modifications are deemed to be within the scope of the present invention as defined by the appended claims. All references cited are specifically incorporated herein in their entirety.

What is claimed is:

1. A sensor comprising:
    an electrode; and
    a cyclodextrin chemically modified to be electrocatalytically active affixed to said electrode.

2. A sensor according to claim 1, wherein the electrode comprises a material selected from the group consisting of glassy carbon, silver and gold.

3. A sensor according to claim 1, wherein the electrode comprises glassy carbon.

4. A sensor according to claim 1, wherein said cyclodextrin comprises at least one imidazole group.

5. A sensor according to claim 1, wherein said cyclodextrin is in the form of a nanotube.

6. A method of detecting a material in a sample, comprising the steps of:
    obtaining a sample which can be detected;
    contacting the sample with a sensor, the sensor comprising an electrode having a cyclodextrin chemically modified to be electrocatalytically active attached thereto; and
    detecting the material.

7. A method according to claim 6, wherein the material to be detected comprises a phenolic ester.

8. A method according to claim 7, wherein the phenolic ester comprises a nitrophenol.

9. A method according to claim 8, wherein the phenolic ester is nitrophenylacetate.

10. A method according to claim 6, wherein the sample comprises a bodily fluid.

11. A method of detecting the presence or absence of a nitrophenyl ester in a sample, comprising the steps of:
    obtaining a sample;
    contacting the sample with a biosensor, wherein the biosensor comprises a cyclodextrin chemically modified to be electrocatalytically active and an electrode; and
    determining the presence or absence of the nitrophenyl ester in the sample.

12. A method according to claim 11, wherein the sample comprises bodily fluids.

13. A method according to claim 11, wherein the chemically modified cyclodextrin comprises an imidazole moiety.

14. A method of constructing a biosensor, comprising the steps of:
    providing an electrode;
    contacting the electrode with a solution, wherein the solution comprises a cyclodextrin chemically modified to be electrocatalytically active; and affixing the electrocatalytically active cyclodextrin to the electrode.

15. A method according to claim 14, wherein the solution comprises PEG.

16. A method according to claim 14, wherein the solution comprises PVP.

17. A method according to claim 14, wherein the electrode is a glassy carbon electrode.

18. A method according to claim 17, wherein the solution comprises PEG.

19. A method according to claim 17, wherein the solution comprises PVP.

20. A method according to claim 17, wherein the solution comprises PEG and PVP.

21. The sensor of claim 1, wherein said cyclodextrin is cross-linked with a polymer.

22. The sensor of claim 21, wherein said polymer comprises polyethylene glycol (PEG).

23. The sensor of claim 21, wherein said polymer comprises polyvinylpyridine (PVP).

24. The sensor of claim 21, wherein said cross-linking is through self-assembly.

25. The sensor of claim 1, said sensor being useful over a pH range of from about 6.50 to about 9.87.

26. The sensor of claim 1, said sensor being bioselective for o-nitrophenyl acetate.

27. The sensor of claim 1, having a fast response time to an analyte with a half life for reduction reaction of about two seconds independent of analyte concentration.

28. The sensor of claim 1, said sensor being mediator free.

29. A sensor for detecting a phenyl ester comprising:
  an electrode; and
  a cyclodextrin chemically modified to be electrocatalytically active.

30. The sensor of claim 29, wherein the phenyl ester to be detected comprises a nitrophenyl ester.

31. The sensor of claim 29, wherein the phenyl ester comprises a nitrophenyl acetate.

* * * * *